United States Patent [19]

Berger et al.

[11] Patent Number: 4,645,844

[45] Date of Patent: Feb. 24, 1987

[54] FUNCTIONALLY SUBSTITUTED PHENOXYALKYL ALKOXYSILANES AND METHOD FOR PREPARING SAME

[75] Inventors: Abe Berger, Summit; Irwin B. Silverstein, Piscataway, both of N.J.

[73] Assignee: M&T Chemicals Inc., Woodbridge, N.J.

[21] Appl. No.: 515,410

[22] Filed: Jul. 20, 1983

Related U.S. Application Data

[60] Continuation of Ser. No. 414,163, Sep. 2, 1982, which is a division of Ser. No. 225,902, Jan. 19, 1981, which is a continuation-in-part of Ser. No. 64,712, Aug. 8, 1979, abandoned, which is a continuation-in-part of Ser. No. 900,197, Apr. 26, 1978, abandoned.

[51] Int. Cl.$^4$ .................... C07D 207/40; C07F 7/08; C07F 7/10; C07F 7/18

[52] U.S. Cl. .................... 548/545; 556/423; 556/422; 556/419; 556/420; 556/445; 556/413; 556/415; 556/428; 556/437; 556/436; 548/482; 548/470; 548/546; 548/536; 546/14

[58] Field of Search ............... 556/423, 422, 419, 420, 556/445, 413, 415, 428, 437, 436; 548/482, 545, 470, 546, 536; 546/14

[56] References Cited

U.S. PATENT DOCUMENTS 4,049,691  9/1977  Meiller ....................... 556/423

Primary Examiner—Paul F. Shaver
Attorney, Agent, or Firm—S. H. Parker; R. B. Bright; J. Matalon

[57] ABSTRACT

Novel and known functionally substituted phenoxyalkyl-, thiophenoxyalkyl- and pyridyloxyalkylsilanes are prepared by reacting substantially equimolar amounts of an alkali- or alkaline earth metal phenoxide, thiophenoxide or pyridyloxide with a haloalkylsilane under anhydrous conditions using a dipolar, aprotic solvent in combination with a liquid hydrocarbon.

17 Claims, No Drawings

FUNCTIONALLY SUBSTITUTED PHENOXYALKYL ALKOXYSILANES AND METHOD FOR PREPARING SAME

This is a continuation of application Ser. No. 414,163, filed Sept. 2, 1982, which in turn is a divisional of application Ser. No. 225,902, filed Jan. 19, 1981; which is in turn a continuation-in-part of application Ser. No. 64,712, filed Aug. 8, 1979, now abandoned; which is in turn, a continuation-in-part of application Ser. No. 900,197, filed Apr. 26, 1978, now abandoned.

BACKGROUND OF THE INVENTION

This invention relates to a new class or organosilicon compounds. More particularly, this invention relates to novel functionally substituted phenoxyalkyl-, thiophenoxyalkyl- and pyridyloxyalkylsilanes and to a method for preparing these compounds. The method is applicable to the preparation of known phenoxyalkylsilanes.

The novel compounds of this invention exhibit the general formula

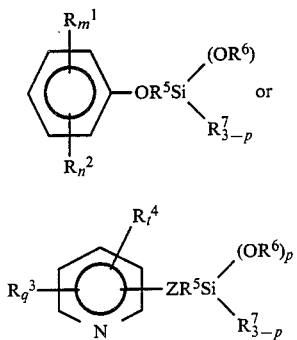

wherein $R^1$ is $-NH_2$, $-NR^8H$, $-NR_2^8$,

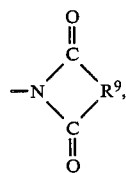

$-CHO$, $-CN$, $-COR^8$, $-COOR^8$, Cl, Br, I,

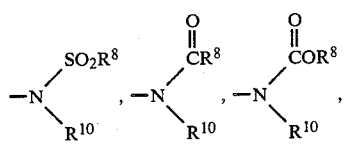

$SO_2R^8$, $-SOR^8$ and $-NO_2$; $R^2$ is alkyl, alkoxy or thioalkoxy and contains from 1 to 12 carbon atoms; $R^3$ is Cl, Br, I, $-COOR^8$, $-CN$, $-NH_2$, $-NR^8H$, $-NR_2^8$,

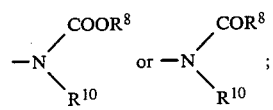

$R^4$ is alkyl containing from 1 to 12 carbon atoms; $R^5$ is methylene or alkylene containing from 3 to 12 carbon atoms; $R^6$ and $R^7$ are individually selected from the group consisting of alkyl, cyanoalkyl, alkenyl, cycloalkyl, aryl, alkaryl and aralkyl, wherein any alkyl group present as all or part of $R^6$ and $R^7$ contains from 1 to 12 carbon atoms; $R^8$ and $R^{10}$ are individually selected from the group consisting of alkyl, cycloalkyl, aryl, alkaryl and aralkyl wherein any alkyl group contains from 1 to 12 carbon atoms; $R^9$ is

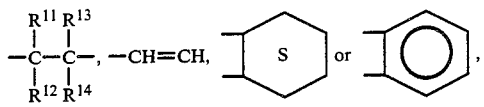

wherein $R^{11}$ and $R^{13}$ are individually selected from the group consisting of hydrogen, chlorine, bromine, iodine and alkyl containing from 1 to 12 carbon atoms; $R^{12}$ and $R^{14}$ are individually selected from the group consisting of hydrogen and alkyl containing from 1 to 12 carbon atoms; Z is oxygen, sulfur,

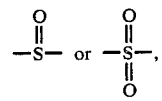

m is an integer from 1 to 5, inclusive; n is 0, 1 or 2, p is 2 or 3, q is 1, 2 or 3 and t is 0 or 1, with the proviso that (a) when m is 2, one or both of $R^1$ are $-NH_2$, $-NR^8H$, $-NR_2^8$,

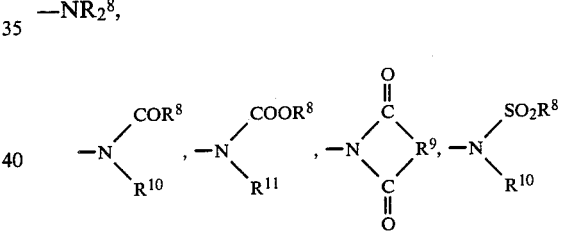

or $-COOR^8$ and any remaining $R^1$ is $-CN$, Cl, Br, I or $-NO_2$; (b) when m is 3 one of $R^1$ is $-NH_2$, $NR^8H$, $-NR_2^8$, or

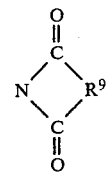

and the remaining two $R^1$ groups are chlorine, bromine or iodine; (c) when m is 4 or 5, $R^1$ is chlorine, bromine or iodine; (d) n is 1 or 2 when m is 1 and $R^1$ is $-NH_2$, $-NO_2$, chlorine, bromine or iodine; and (e) the sum of m and n is equal to or less than 5.

This invention also provides a method for preparing the aforementioned novel compounds in addition to known phenoxyalkyl- and thiophenoxyalkyl silanes, said method consisting of reacting a haloalkylsilane of the general formula

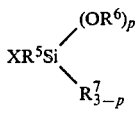

with an anhydrous alkali- or alkaline earth metal phenoxide or thiophenoxide of the formula

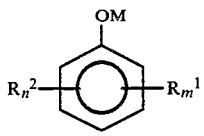

or an anhydrous alkali- or alkaline earth metal salt of a hydroxy- or mercaptopyridine of the formula

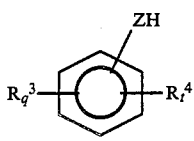

at a temperature of from ambient to 200° C. under an inert atmosphere and in the presence of a liquid reaction medium consisting essentially of at least one dipolar, aprotic liquid, and, optionally, at least one liquid hydrocarbon boiling from 40° to 200° C. under ambient pressure, maintaining the resultant reaction mixture at a temperature of from 40° to 200° C. for a period of time sufficient to form the desired silane and isolating the silane from said reaction mixture. The present method is applicable to the preparation of known silanes containing functional groups, including the aminophenoxypropyl silanes disclosed in U.S. Pat. No. 4,049,691, the pertinent portions of which are hereby incorporated by reference.

DETAILED DESCRIPTION OF THE INVENTION

The novel compounds of this invention are functionally substituted phenoxy-, pyridyloxy and thiopyridyloxyalkylsilanes of the general formulae disclosed in the preceding section of this specification. The functional substituent on the phenyl group, represented by $R^1$ in the general formula, can be $-NH_2$, $-NR^8H$, $-NR_2^8$,

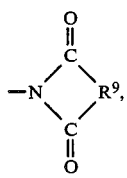

—CHO, —CN, —COR$^8$, —COOR$^8$, Cl, Br, I,

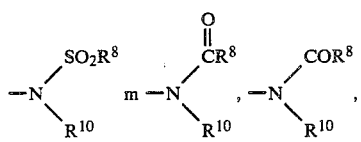

—SO$_2$R$^8$, —SOR$^8$ and —NO$_2$. The various substituents represented by $R^1$ and $R^{10}$ are defined in the preceding section of this specification. Amino groups are the preferred substituent because of the many useful applications of this class of compounds. The substituent can be located ortho, meta or para with respect to the oxygen or sulfur atom represented by Z in the foregoing formula. The phenoxy, pyridyloxy or thiopyridyloxy group is joined to the silicon atom by means of an alkylene group that can methylene or a higher alkylene group containing from 3 to 12 carbon atoms in either a liner or branched configuration. Compounds wherein $R^5$ is ethylene have been found to be unstable in the presence of even trace amounts of aqueous acids or bases as to be useless for all practical purposes. In addition to the aformentioned alkylene group the silicon atom is also bonded to three alkoxide or aryloxide group represented by $OR^6$ in the foregoing formula or to two alkoxide or aryloxide groups and one hydrocarbyl or cyanoalkyl group. The term "hydrocarbyl" includes alkyl, cycloalkyl, aryl, alkaryl and aralkyl, as previously defined for $R^6$ and $R^7$.

Both the present compounds and known phenoxyalkyl and thiophenoxyalkyl silanes are prepared by reacting an alkali metal- or alkaline earth metal salt, preferably the sodium or potassium salt, of the desired phenol, thiophenol, hydroxypyridine or thiopyridine with a haloalkylsilane of the general formula

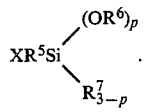

This reaction is highly exothermic and is preferably conducted under an inert atomsphere and in the in the absence of even trace amounts of water, since water is known to react readily with silanes containing 2 or 3 alkoxy or aryloxy groups bonded to silicon to yield polymeric products. The reaction medium is a dipolar, aprotic liquid such as dimethyl sulfoxide, N,N-dimethylformamide, tetramethylurea, N-methyl pyrolidone or hexamethylphosphoramide. The dipolar, aprotic liquid constitutes from 1 to about 100% by weight of the reaction medium, preferably from 20 to 50% by weight. Any remaining portion of the reaction medium consists esstentionally of at least one liquid hydrocarbon boiling from 40° to about 200° C. under atmospheric pressure. The purpose of the liquid hydrocarbon is to facilitate the removal by azeotropic distillation of any water present in the reaction mixture. Preferably, the haloalkylsilane is gradually added to a reaction mixture containing the alkali meta salt. When the addition is complete and any exothermic reaction has subsided, it is usually desirable to heat the reaction mixture at from 70° to about 150° C. for several hours to ensure substantially complete conversion of the reactants to the desired functionally substituted phenoxyalkyl-, thiophenoxyalkyl-, thiopyridyloxyalkyl- or pyridyloxyalkylsilane. The present compounds, many of which are colorless, high-boiling, viscous oils, are soluble in the reaction medium and readily isolatable by removal of the aforementioned liquid hydrocarbon and dipolar liquid. Some of the compounds may darken if exposed to light or air for extended periods of time.

As previously disclosed the present method is applicable to the preparation of any phenoxyalkylsilane, some of which are known compounds.

The tri(hydrocarbyloxy)haloalkylsilanes or di(hydrocarbyloxy)haloalkylsilanes employed as one of the reagents for preparing the present compounds are either commercially available or can readily be obtained by reacting the corresponding haloalkyltrihalosilane or a silane of the formula

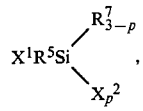

wherein $X^1$ and $X^2$ are chlorine, bromine or iodine, with an alcohol, $R^6OH$, that contains from 1 to 12 carbon atoms. Alternatively, the hydroxyl group can be bonded to a carbocyclic or heterocyclic ring structure such as a cyclohexyl or phenyl group. The haloalkyltrihalosilane can be prepared by reacting a haloalkene such as allyl chloride or methallyl chloride with a trihalosilane, $HSiX_3^2$, at ambient temperature in the presence of a platinum catalyst. Procedures for preparing the intermediate silanes are well known in the art. A detailed discussion of reaction conditions is therefore not required in this specification.

Illustrative of the preferred functionally substituted phenols and thiophenols that can be employed to prepare the present compounds are aminophenols, aminothiophenols and aminochlorophenols wherein the amino group is located in the ortho, meta or para position relative to the hydroxyl group, the isomeric hydroxybenzaldehydes and the isomeric esters of hydroxybenzoic and mercaptobenzoic acids wherein the alcohol residue of the ester contains from 1 to 12 carbon atoms. If the alcohol contains a phenyl group, the number of carbon atoms is from 7 to 18. Other functional substituents that can be present on the phenyl group are disclosed in the present specification and claims. In addition the phenyl group may contain 1 or 2 alkyl, cycloalkyl or aryl groups.

Alternatively, the amino group of an aminophenol or aminothiophenol can be prereacted to form an amide, imide, carbamate, sulfonamide or other group prior to reaction of the phenol or thiophenol, in the form of its alkali metal or alkaline earth metal salt, with the haloalkylalkoxysilane.

An anhydrous form of the alkali metal or alkaline earth metal salt of the phenol, thiophenol, hydroxypyridine or mercaptopyridine can be prepared by employing the free metal or a hydride or alkoxide of the metal, such as sodium hydride or methoxide. Any of these compounds are added to a solution of the desired phenol, thiophenol or pyridine derivative in a dipolar aprotic liquid which may optionally contain a liquid hydrocarbon. The metal, metal hydride or metal alkoxide is conveniently employed as a dispersion or slurry in a liquid hydrocarbon. The temperature of the reaction medium is maintained between ambient and about 50° C. to avoid an uncontrollable exothermic reaction.

The functionally substituted silanes of this invention are useful as coupling agents for bonding an organic polymer to an inorganic material such as glass fibers or metal, as flocculating agents for water purification, as sizings for glass fibers or fabrics and as an ingredient in polishes and waxes, particularly for automobiles. The present compounds can be reacted with liquid hydroxy- or alkoxy-terminated organopolysiloxanes together with optional fillers to form elastomeric products that are useful as coating materials, sealants and molding compositions. Compounds wherein $R^1$ of the foregoing formula is amino or dialkylamino ($-NH_2$ or $-NR_2^4$) impart detergent resistance to waxes and polishes.

The following examples disclose preferred embodiments of the present compounds and should not be interpreted as limiting the scope of the accompanying claims. All parts and percentages are by weight unless otherwise specified.

EXAMPLE 1

Preparation of 3(p-aminophenoxy)propyl Trimethoxysilane

A glass reactor was charged with 60 (g) (0.55 mole) p-aminophenol, 43.28 g of a 50% aqueous solution of sodium hydroxide (0.54 mole NaOH), 112 cc dimethylsulfoxide and 120 cc toluene. The resultant mixture was heated to the boiling point for six hours under a nitrogen atmosphere to remove all of the water present by azeotropic distillation. The reaction mixture was then allowed to cool to about 75° C., at which time 109 g (0.55 mole) of 3-chloropropyl trimethoxysilane was added dropwise while the reaction mixture was stirred. The temperature of the reaction mixture increased spontaneously to 85° C. during this addition. The temperature of the reaction mixture was maintained at from 75° to 85° C. by heating and control of the addition rate. Following completion of the addition, the reaction mixture was heated at 115° C. for 16 hours, following which the mixture was allowed to cool and was filtered to remove any solid material. The solvents were then removed under a pressure of about 15 mm of mercury at a temperature of about 60° C. The pressure was then reduced to from 3 to 4 mm of mercury and the material boiling from 170° to 180° C. was recovered. This fraction, which weighed 70 g, was distilled using a fractionating column and a 50 g portion boiling from 175° to 177° C. under a pressure of 3 mm of mercury, was collected. The colorless liquid was found to contain 10.19% silicon and 5.20% nitrogen. The calculated values for 3(p-aminophenoxy)propyl trimethoxy silane are 10.33% silicon and 5.17% nitrogen. The infrared and nuclear magnetic resonance spectra of the product were in agreement with the proposed structure.

EXAMPLE 2

Preparation of 3(m-aminophenoxy)propyl Trimethoxysilane

Using the general procedure described in the preceding Example 1, a reactor was charged with 300 g (2.75 mole) m-aminophenol, 560 cc dimethylsulfoxide, 600 cc toluene and 216 cc of a 50% aqueous solution of sodium hydroxide (2.70 moles NaOH). The water present in the reactor was removed by azeotropic distillation under a nitrogen atmosphere at a temperature of 120° C. The temperature of the reaction mixture was then lowered to 90° C. and maintained at about this value during the gradual addition of 545 g (2.75 mole) of 3-chloropropyl trimethoxysilane. Following completion of the addition, which required 2 hours, the reaction mixture was heated at the boiling point for 16 hours. The product was recovered and fractionally distilled as described in the preceding example. The fraction boiling from 178° to 180° C. at a pressure of 3 mm of mercury was collected and weighed 630 g (85% yield). The infrared and nuclear magnetic resonance spectra of the distillate confirm the proposed structure

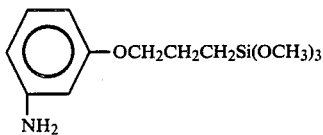

A vapor phase chromatogram of the product indicated a purity of greater than 98%.

EXAMPLE 3

Preparation of 3(p-formylphenoxy)propyl Trimethoxysilane

Using the general procedure described in the preceding Example 1, a reactor was charged with 62.2 g (0.55 mole) p-hydroxybenzaldehyde, 112 cc dimethylsulfoxide, 120 cc toluene and 43.2 g of a 50% aqueous sodium hydroxide solution containing 0.54 mole NaOH. All of the water present was removed by azeotropic distillation at a temperature of about 110° to 115° C. The reaction mixture was heated to the boiling point during the gradual addition of 109 g (0.55 mole) of 3-chloropropyl trimethoxysilane. The product, 3(p-formylphenoxy)propyl trimethoxysilane, was isolated by filtration and removal of the solvents from the recovered liquid phase under reduced pressure, followed by fractional distillation of the residue. The fraction boiling at 208° C. at a pressure of 3 mm of mercury was collected (85% yield, based on silane). The infrared and nuclear magnetic resonance spectra of the distillate confirm the proposed structure

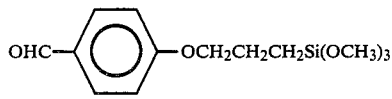

The vapor phase chromatogram of the product indicated a purity of greater than 98%.

EXAMPLE 4

Preparation of 3(m-diethylaminophenoxy)propyl Trimethoxysilane

Using the general procedure described in the preceding Example 1, a reactor was charged with 90.75 g (0.55 mole) m-diethylaminophenol, 112 cc dimethylsulfoxide, 120 cc toluene and 43.28 g of a 50% aqueous sodium hydroxide solution. All of the water present in the reactor was removed by azeotropic distillation. The reaction mixture was allowed to cool to 80° C., at which time 109 g (0.55 mole) of chloropropyl trimethoxysilane were gradually added over a period of 2 hours. The temperature of the reaction mixture increased to 88° C. during the addition. Following completion of the addition, external heating was applied to maintain the temperature of the reaction mixture at 80° C. for 16 hours. The reaction mixture was then allowed to cool and was filtered. The liquid phase was recovered and evaporated under a pressure of 5 mm of mercury to remove the toluene and dimethylsulfoxide. The pressure inside the reactor was reduced to 2 mm and the product, 3(m-diethylaminophenoxy)propyl trimethoxysilane, distilled at a temperature of 185°–187° C. Analysis by vapor phase chromatography demonstrated that the product was 97% pure.

EXAMPLE 5

Preparation of 3(3-pyridyloxy)propyl Trimethoxysilane

Using the general procedure described in Example 1, a reactor was charged with 52.3 g (0.55 mole) 3-hydroxypyridine, 112 cc dimethylsulfoxide, 120 cc toluene and 43.2 g of a 50% aqueous sodium hydroxide solution. The water present in the reactor was removed by azeotropic distillation over a period of 64 hours. The temperature of the reaction mixture was maintained at from 85° to 105° C. during this time period. A 109 g portion of 3-chloropropyl trimethoxysilane was gradually added while the temperature of the reaction mixture was maintained at 95° C. This temperature was maintained for 7 hours, at which time a vapor phase chromatogram of the reaction mixture indicated that the reaction was substantially complete. The reaction mixture was then filtered and the diluents (toluene and dimethylsulfoxide) evaporated under a pressure of 5 mm of mercury. The product, 3(3-pyridyloxy)propyl trimethoxysilane, distilled at a temperature of 142° C. under a pressure of 1 mm of mercury. Analysis using vapor phase chromatography demonstrated that the product was 97% pure.

EXAMPLE 6

Preparation of m-aminophenoxypropyl Methyldimethoxysilane

Using the general procedure described in Example 1 a reactor was charged with 60 g (0.55 mole) of p-aminophenol, 43.28 g of a 50% by weight aqueous solution of sodium hydroxide (0.54 mole NaOH), 112 cc dimethylsulfoxide and 120 cc toluene. The resultant mixture was heated to the boiling point for six hours under a nitrogen atmosphere to remove all of the water present by azeotropic distillation. The reaction mixture was then allowed to cool to about 75° C., at which time 100.4 g (0.56 mole) of 3-chloropropyl methyldimethoxysilane was added dropwise while the reaction mixture was stirred. Following completion of the addition the reaction mixture was heated at 115° C. for about 16 hours, following which the mixture was allowed to cool and was filtered to remove any solid material. The solvents were then removed under a pressure of about 15 mm of mercury at a temperature of about 60° C. The pressure was then reduced to from 3 to 4 mm of mercury and the material boiling from 230° to 235° C. was removed. This fraction weighed 112 g, equivalent to a yield of 80% based on starting materials. Analysis by vapor phase chromatography indicated that the purity of the product was greater than 98%. The infrared and nuclear magnetic resonance spectra of the product were consistent with the proposed structure.

EXAMPLE 7

Preparation of 3,5 Bis(carbomethoxy)phenoxypropyl Trimethoxysilane

Using the general procedure described in Example 1 a reactor was charged with 115.5 g (0.55 mole) 3,5 bis(carbomethoxy)phenol, 43.28 g of a 50% by weight aqueous solution of sodium hydroxide (equivalent to 0.54 mole NaOH), 112 cc dimethylsulfoxide and 1200 cc toluene. The resultant mixture was heated at the boiling point under a nitrogen atmosphere for 6 hours to remove substantially all of the water present by azeotropic distillation. The reaction mixture was then allowed to cool to about 75° C., at which time 109 g (0.555 mole) of chloropropyl trimethoxysilane were added dropwise to the reaction mixture. Upon completion of this addition the temperature of the reaction mixture was increased to 115° C. and maintained at this level for about 16 hours, at which time the reaction mixture was allowed to cool to ambient temperature. The reaction mixture was then filtered and the toluene, dimethylsulfoxide and other volatile materials were removed under the reduced pressure produced by a water aspirator. The liquid residue was then distilled under a pressure of from 3 to 4 mm of mercury and the fraction boiling from 240° to 270° C. was collected and weighed 95 g. Fractional distillation of this material yielded 75 g of a viscous, colorless oil that was collected over the boiling range from 250° to 252° C. under a pressure of 3 mm of mercury. The infrared and nuclear magnetic resonance spectra of the product were consistent with the proposed structure. The vapor phase chromatogram indicated that the product was at least 98% pure. The product gradually solidified upon standing.

EXAMPLE 8

Preparation of 3[o-(2-propenyl)phenoxy]propyl trimethoxysilane

Using the general procedure described in Example 1 a reactor was charged with 73.7 g (0.55 mole) of o-allylphenol, 43.28 g of a 50% by weight aqueous solution of sodium hydroxide (0.54 mole NaOH), 112 cc dimethylsulfoxide and 120 cc toluene. The resultant mixture was heated to the boiling point for six hours under a nitrogen atmosphere to remove all of the water present by azeotropic distillation. The reaction mixture was then allowed to cool to about 75° C., at which time 109 g (0.56 mole) of 3-chloropropyl trimethoxysilane was added dropwise while the reaction mixture was stirred. Following completion of the addition the reaction mixture was heated at 115° C. for about 16 hours, following which the mixture was allowed to cool and was filtered to remove any solid material. The solvents were then removed under a pressure of about 15 mm of mercury at a temperature of about 60° C. The pressure was then reduced to 2 mm of mercury and the material boiling at 146° C. was collected. The weight of this fraction was equivalent to a yield of 90% based on starting materials. Analysis by vapor phase chromatography indicated that the purity of the product was greater than 98%. The infrared and nuclear magnetic resonance spectra of the product were consistent with the proposed structure.

EXAMPLE 9

Preparation of m-aminophenoxy-2-methylpropyl Methyldimethoxysilane

Using the general procedure described in Example 1 a reactor is charged with 60 g (0.55 mole) of p-aminophenol, 43.28 g of a 50% by weight aqueous solution of sodium hydroxide (0.54 mole NaOH), 112 cc dimethylsulfoxide and 120 cc toluene. The resultant mixture is heated to the boiling point for six hours under a nitrogen atmosphere to remove all of the water present by azeotropic distillation. The reaction mixture is then allowed to cool to about 75° C., at which time 117 g (0.56 mole) of 2-methylchloropropyl methyldimethoxysilane are added dropwise while the reaction mixture is stirred. Following completion of the addition the reaction mixture is heated at 115° C. for about 16 hours, following which the mixture is allowed to cool and is filtered to remove any solid material. The solvents are then removed under a pressure of about 15 mm of mercury at a temperature of about 60° C. The pressure is then reduced to 2 mm of mercury and the material boiling at 165° C. is collected. Analysis by vapor phase chromatography indicates that the purity of the product, a pale yellow viscous liquid, was greater than 98%.

EXAMPLE 10

Preparation of p-carbomethoxyphenoxypropyl methyldimethoxysilane

Using the general procedure described in Example 1 a reactor was charged with 83.7 g (0.55 mole) of methyl-p-hydroxybenzoate, 43.28 g of a 50% by weight aqueous solution of sodium hydroxide (0.54 mole NaOH), 112 cc dimethylsulfoxide and 120 cc toluene. The resultant mixture was heated to the boiling point for six hours under a nitrogen atmosphere to remove all of the water present by azeotropic distillation. The reaction mixture was then allowed to cool to about 75° C. at which time 109 g (0.56 mole) of 3-chloropropyl trimethoxysilane were added dropwise while the reaction mixture was stirred. Following completion of the addition the reaction mixture was heated at 115° C. for about 16 hours, following which the mixture was allowed to cool and was filtered to remove any sold material. The solvents were then removed under a pressure of about 15 mm of mercury at a temperature of about 60° C. The pressure was then reduced to 2 mm of mercury and the material boiling from 230° to 235° C. was collected. The weight of this fraction was equivalent to a yield of 92% based on starting materials. Analysis by vapor phase chromatography indicated that the purity of the product was greater than 98%. The infrared and nuclear magnetic resonance spectra of the product was consistent with the proposed structure.

EXAMPLE 11

Preparation of m-Succinimidophenoxypropyl Trimethoxysilane

A solution containing 200 g of succinic anhydride, 218 g m-aminophenol and one liter of glacial acetic acid was heated at the boiling point for 16 hours in a reactor equipped with a mechanically driven stirrer and a water-cooled reflux condenser. The reaction mixture solidified upon cooling to ambient temperature. The solid was pulverized, washed with water to remove the acetic acid, then dried. The resultant m-succinimidophenol (105.1 g, 0.55 mole) together with 43.28 g of a 50% by weight aqueous solution of sodium hydroxide, 112 cc dimethylsulfoxide and 120 cc toluene were placed in a reactor equipped with a nitrogen inlet, water-cooled reflux condenser and Dean-Stark trap. The resultant mixture was heated to the boiling point for six hours under a nitrogen atmosphere to remove all of the water present by azeotropic distillation. The reaction mixture was then allowed to cool to about 75° C., at which time 109 g (0.56 mole) of 3-chloropropyl trimethoxysilane was added dropwise while the reaction mixture was stirred. Following completion of the addition the reaction mixture was heated at 115° C. for about 16 hours, following which the mixture was allowed to cool and was filtered to remove any solid material. The solvents were then removed under a pressure of about 15 mm of mercury at a temperature of about 60° C. The pressure was then reduced to 0.5 mm of mercury and the material boiling at 228° C. was collected. Analysis by vapor phase chromatography indicated that the purity of the product, a white solid, was greater than 98%. The infrared and nuclear magnetic resonance spectra of the product were consistent with the proposed structure.

EXAMPLE 12

Attempted Preparation of p-aminophenoxypropyl trimethoxy silane in the absence of a dipolar aprotic solvent A glass reactor was charged with 120 g (0.9 mole) p-aminphenol, 464 cc toluene and 86.6 g of a 50% by weight aqueous solution of sodium hydroxide. The resultant mixture was heated at the boiling point to remove the water present in the reaction mixture by azeotropic distillation. The temperature of the reaction mixture was then reduced to 81° C. and 178.2 g (0.9 mole) of 3-chloropropyl trimethoxysilane were added dropwise over a period of one hour. The reaction mixture was then heated at 81° C. for 16 hours with stirring, during which time a solid accumulated on the inner wall of the reactor. The toluene and other volatile materials were removed by heating the reaction mixture under the reduced pressure produced by a water aspirator. The residue, a clear yellow liquid, exhibited an infrared spectrum which did not contain the absorption maximum characteristic of the amino group. The boiling point of this product (45° C. under a pressure of 2 mm of mercury) demonstrated that it was, in fact, unreacted 3-chloropropyl trimethoxysilane.

What is claimed is:

1. A silane represented by the general formula $$\underset{R^2_n}{\overset{R^1_m}{\bigcirc}}\text{—OR}^5\text{Si}\underset{R^7_{3-p}}{\overset{(OR^6)_p}{<}}$$

where
$R^1$ is $-NH_2$, $-NR^8H$, $-NR_2^8$, $$-N\begin{matrix}\overset{O}{\overset{\|}{C}}\\ \underset{\|}{\underset{O}{C}}\end{matrix}R^9,$$

$-CHO$, $-CN$, $-COR^8$, $-COOR^8$, Cl, Br, I, alkenyl which contains from 2 to 10 carbon atoms, and $-NO_2$;
$R^2$ is alkyl, alkoxy or thioalkoxy and contains from 1 to 12 carbon atoms;

$R^5$ is methylene or alkylene containing from 3 to 12 carbon atoms;
$R^6$ and $R^7$ are individually selected from the group consisting of alkyl, cyanoalkyl, alkenyl, cycloalkyl, aryl, alkaryl and aralkyl, wherein any alkyl group present as all or part of $R^6$ and $R^7$ contains from 1 to 12 carbon atoms;
$R^8$ is selected from the group consisting of alkyl, cycloalkyl, aryl, alkaryl and aralkyl wherein any alkyl group contains from 1 to 12 carbon atoms;
$R^9$ is $$-\underset{\underset{R^{12}}{|}\underset{R^{14}}{|}}{\overset{\overset{R^{11}}{|}\overset{R^{13}}{|}}{C-C-}}, -CH=CH, \bigcirc, \overset{S}{\bigcirc} \text{ or } \bigcirc\!\!\!\bigcirc,$$

wherein
$R^{11}$ and $R^{12}$ are individually selected from the group consisting of hydrogen, chlorine, bromine, iodine and alkyl containing from 1 to 12 carbon atoms;
$R^{12}$ and $R^{14}$ are individually selected from the group consisting of hydrogen and alkyl containing from 1 to 12 carbon atoms;
m is an integer equal to 1;
n is 0, 1 or 2;
p is 2 or 3;
with the proviso that if $R^1$ is $-NH_2$ or $-NO_2$, then n is 1 or 2.

2. A silane according to claim 1 wherein $R^1$ is $-NH_2$, $-NR_2^8$ or $-CHO$.

3. A silane according to claim 1 wherein $R^5$ is propylene.

4. A silane according to claim 1 wherein $R^6$ and $R^7$ are alkyl and contain from 1 to 4 carbon atoms.

5. A silane according to claim 4 wherein $R^6$ and $R^7$ are methyl.

6. A silane according to claim 1 wherein n is 0 or 1.

7. A silane according to claim 1 wherein n is 1 and $R^2$ is methyl.

8. A silane according to claim 1 which is 3(p-formylphenoxy)propyl trimethoxysilane.

9. A silane according to claim 1 which is 3(m-diethylaminophenoxy)propyl trimethoxysilane.

10. A silane according to claim 1 which is 3(3-pyridyloxy)propyl trimethoxysilane.

11. A silane according to claim 1 which is 3,5 bis-(carbomethoxy)phenoxypropyl trimethoxysilane.

12. A silane according to claim 1 which is 3[o-propenyl)phenoxy]propyl trimethoxysilane.

13. A silane according to claim 1 which is p-carbomethoxyphenoxypropyl methyldimethoxysilane.

14. A silane according to claim 1 which is m-succinimidophenoxypropyl trimethoxysilane.

15. A silane according to claim 1 in which $R^1$ is alkenyl which contains from 2 to 10 carbon atoms.

16. A silane according to claim 1 wherein $R^1$ is $CH_3COO-$, and n is 0.

17. A silane according to claim 1 wherein $R^2$ is alkyl and n is 2.

* * * * *